US012741140B2

(12) United States Patent
Deslauriers

(10) Patent No.: US 12,741,140 B2
(45) Date of Patent: Sep. 22, 2026

(54) WIRELESS TRANSDUCER ARRAYS APPLYING TUMOR TREATING FIELDS AND SYSTEMS AND METHODS OF USE THEREOF

(71) Applicant: Novocure GmbH, Root (CH)

(72) Inventor: Richard Deslauriers, Woodbury, CT (US)

(73) Assignee: Novocure GmbH, Baar (CH)

( * ) Notice: Subject to any disclaimer, the term of this patent is extended or adjusted under 35 U.S.C. 154(b) by 335 days.

(21) Appl. No.: 18/533,467

(22) Filed: Dec. 8, 2023

(65) Prior Publication Data

US 2024/0189587 A1 Jun. 13, 2024

Related U.S. Application Data

(60) Provisional application No. 63/387,113, filed on Dec. 13, 2022.

(51) Int. Cl.
*A61N 1/32* (2006.01)
*A61N 1/08* (2006.01)

(52) U.S. Cl.
CPC .................................... *A61N 1/32* (2013.01); *A61N 1/08* (2013.01)

(58) Field of Classification Search
CPC ... A61N 1/32; A61N 1/08; A61N 1/06; A61N 1/36002
See application file for complete search history.

(56) References Cited

U.S. PATENT DOCUMENTS 11,090,491 B2 8/2021 Mishra et al.
2016/0022986 A1* 1/2016 Travers .................... A61N 1/32
2016/0087687 A1* 3/2016 Kesler ..................... H02J 50/80 307/104

(Continued)

FOREIGN PATENT DOCUMENTS

WO WO2015/092747 A2 6/2015
WO WO 2022/076510 4/2022
WO WO2022/137019 A1 6/2022

OTHER PUBLICATIONS

PCT, International Search Report & Written Opinion, dated Mar. 26, 2024, regarding international application No. PCT/IB2023/062410, 11 pages.

*Primary Examiner* — Catherine M Voorhees
(74) *Attorney, Agent, or Firm* — DUNLAP CODDING , P.C.

(57) ABSTRACT

A transducer array, tumor treating field system, and method are herein disclosed. The tumor treating field system comprises an electric field generator configured to generate a first electrical signal having an alternating current waveform at a frequency in a range from 50 kHz to 1 MHz; a transmitter circuitry electrically coupled to the electric field generator and operable to receive the first electrical signal and transmit a wireless signal; a receiver circuitry operable to receive the wireless signal and output a second electrical signal having the alternating current waveform; a first transducer array electrically coupled to the receiver circuitry; and a second transducer array electrically coupled to the receiver circuitry. The first transducer array and the second transducer array are configured to generate an alternating electric field based on the alternating current waveform of the second electrical signal received from the receiver circuitry.

10 Claims, 6 Drawing Sheets

(56) References Cited

U.S. PATENT DOCUMENTS

2022/0176102 A1* 6/2022 Pribula .............. A61N 1/36002
2022/0288405 A1* 9/2022 Wasserman .......... A61N 1/0496
2023/0147179 A1* 5/2023 Sawa ........................ G01S 3/42
307/104

* cited by examiner

WIRELESS TRANSDUCER ARRAYS APPLYING TUMOR TREATING FIELDS AND SYSTEMS AND METHODS OF USE THEREOF

CROSS-REFERENCE TO RELATED APPLICATIONS

This application claims priority to the provisional patent application identified by U.S. Ser. No. 63/387,113, filed Dec. 13, 2022, the entire content of which is hereby expressly incorporated herein by reference.

BACKGROUND OF THE ART

Tumor Treating Fields (TTFields or TTFs) are low intensity (e.g., 1-3 V/cm) alternating electric fields within the intermediate frequency range (e.g., 50 kHz to 1 MHz, such as 50-500 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the transducer arrays that make up each of these pairs are positioned on opposite sides of the body part that is being treated. More specifically, for the OPTUNE® system, one pair of electrodes of the transducer array is located to the left and right (LR) of the tumor, and the other pair of electrodes of the transducer array is located anterior and posterior (AP) to the tumor. TTFields are approved for the treatment of glioblastoma multiforme (GBM), and may be delivered, for example, via the OPTUNE® system (Novocure Limited, St. Helier, Jersey), which includes transducer arrays placed on the patient's shaved head. More recently, TTFields therapy has been approved as a combination therapy with chemotherapy for malignant pleural mesothelioma (MPM), and may find use in treating tumors in other parts of the body.

The transducer arrays are placed on the patient at target locations determined to have a high therapeutic value to treat the patient. The device is intended to be continuously worn by the patient for 2-4 days before removal for hygienic care and re-shaving (if necessary), followed by reapplication with a new set of arrays. The numerous arrays and sensors on each array require a large number of wires connecting to an electric field generator. The number of wires increases the weight of the system supported by the patient, which may become uncomfortable over the extended periods of time the system is used.

SUMMARY OF THE INVENTION

Thus, a need exists for a new and improved transducer array that reduces or eliminates the wires needed to connect the transducer array to the electric field generator. It is to such systems and methods of producing and using the same, that the present disclosure is directed.

The problem of limiting movement of the transducer array from the target area on the patient is solved by a transducer array, a tumor treating field system, and method of production and use thereof. In one embodiment, the tumor treating field system comprises an electric field generator configured to generate a first electrical signal having an alternating current waveform at a frequency in a range from 50 kHz to 1 MHz; a transmitter circuitry electrically coupled to the electric field generator and operable to receive the first electrical signal and transmit a wireless signal; a receiver circuitry operable to receive the wireless signal and output a second electrical signal having the alternating current waveform; a first transducer array electrically coupled to the receiver circuitry; and a second transducer array electrically coupled to the receiver circuitry. The first transducer array and the second transducer array are configured to generate an alternating electric field based on the alternating current waveform of the second electrical signal received from the receiver circuitry.

The details of one or more implementations of the subject matter described in this specification are set forth in the accompanying drawings and the description below. Other aspects, features and advantages of the subject matter will become apparent from the description, the drawings, and the claims.

BRIEF DESCRIPTION OF THE DRAWINGS

The accompanying drawings, which are incorporated in and constitute a part of this specification, illustrate one or more implementation described herein. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figures 1, 2, 3:
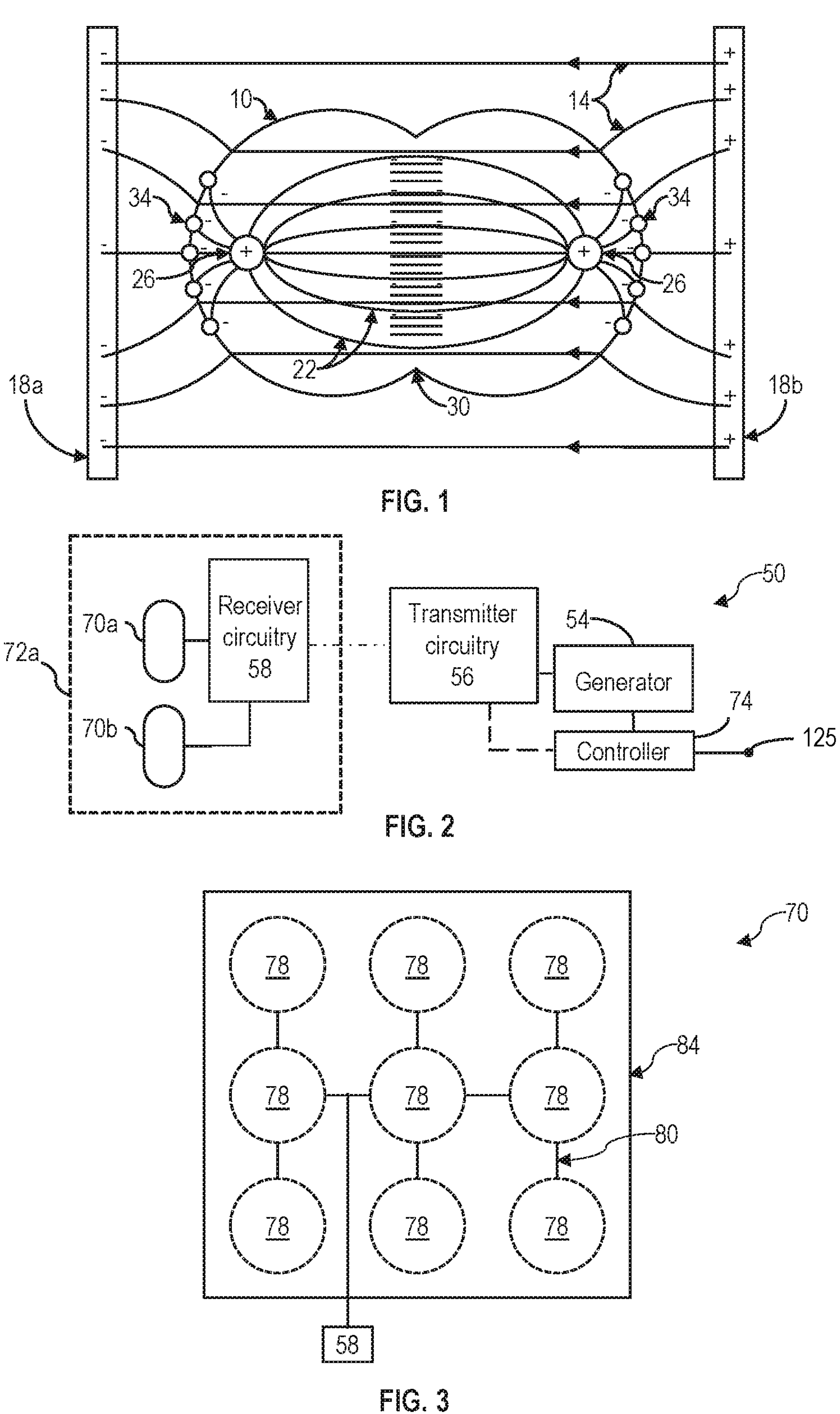
FIG. 1 is an exemplary embodiment of a schematic diagram of electrodes as applied to living tissue.
FIG. 2 is an exemplary embodiment of an electronic device configured to generate a TTField constructed in accordance with the present disclosure.
FIG. 3 is a block diagram of an exemplary embodiment of a transducer array constructed in accordance with the present disclosure.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Headings are provided for convenience only and are not to be construed to limit the disclosure in any manner. Embodiments illustrated under any heading or in any portion of the disclosure may be combined with embodiments illustrated under the same or any other heading or other portion of the disclosure. Any combination of the elements described herein in all possible variations thereof is encompassed by the disclosure unless otherwise indicated herein or otherwise clearly contradicted by context.

Unless otherwise required by context, singular terms shall include pluralities and plural terms shall include the singular.

All of the compositions, assemblies, systems, kits, and/or methods disclosed herein can be made and executed without undue experimentation in light of the present disclosure. Where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

The use of the term “a” or “an” when used in conjunction with the term “comprising” in the claims and/or the specification may mean “one,” but is also consistent with the meaning of “one or more,” “at least one,” and “one or more than one.” The term “plurality” refers to “two or more.”

In addition, the use of the term “at least one of X, Y, and Z” will be understood to include X alone, Y alone, and Z alone, as well as any combination of X, Y, and Z. The use of ordinal number terminology (e.g., “first,” “second,” “third,” “fourth,” etc.) is solely for the purpose of differentiating between two or more items and is not meant to imply any sequence or order or importance to one item over another or any order of addition, for example.

The use of the term “or” in the claims is used to mean an inclusive “and/or” unless explicitly indicated to refer to alternatives only or unless the alternatives are mutually exclusive.

Circuitry, as used herein, may be analog and/or digital components, or one or more suitably programmed processors (e.g., microprocessors) and associated hardware and software, or hardwired logic. Also, “components” may perform one or more functions. The term “component,” may include hardware, such as a processor (e.g., microprocessor), an application specific integrated circuit (ASIC), a field programmable gate array (FPGA), a combination of hardware and software, and/or the like. The term “processor” as used herein means a single processor or multiple processors working independently or together to collectively perform a task.

As used herein, all numerical values or ranges include fractions of the values and integers within such ranges and fractions of the integers within such ranges unless the context clearly indicates otherwise. The numerical ranges specified herein includes the endpoints, and all values, sub-ranges of values within the range, and fractions of the values and integers within said range. Thus, any two values within the range of 1 mm to 10 m, for example, can be used to set a lower and an upper boundary of a range in accordance with the embodiments of the present disclosure.

As used herein, the term TTField (TTFields, or TTF(s)) refers to low intensity (e.g., 1-4 V/cm) alternating electric fields of medium frequencies (about 50 kHz-1 MHz, and more preferably from about 50 kHz-500 kHz) that when applied to a conductive medium, such as a human body, via electrodes may be used, for example, to treat tumors as described in U.S. Pat. No. 7,016,725, 7,089,054, 7,333,852, 7,565,205, 7,805,201, and 8,244,345 by Palti, the entire contents of which are hereby incorporated herein in their entirety, and in a publication by Kirson (see Eilon D. Kirson, et al., Disruption of Cancer Cell Replication by Alternating Electric Fields, Cancer Res. 2004 64:3288-3295). TTFields have been shown to have the capability to specifically affect cancer cells and serve, among other uses, for treating cancer. TTFields therapy is an approved mono-treatment for recurrent glioblastoma (GBM), and an approved combination therapy with chemotherapy for newly diagnosed GBM patients.

As used herein, the term TTSignal is an electrical signal that, when received by electrodes applied to a conductive medium, such as a human body, causes the electrodes to generate the TTField described above. The TTSignal is often an AC, or alternating current waveform, electrical signal.

Referring now to the drawings and in particular to FIG. 1, shown therein is an exemplary embodiment of a dividing cell 10, under the influence of external TTFields, generally indicated as lines 14, generated by a first electrode **18*a* having a negative charge and a second electrode 18*b* having a positive charge. Further shown are microtubules 22 that are known to have a very strong dipole moment. This strong polarization makes the microtubules 22, as well as other polar macromolecules and especially those that have a specific orientation within the cell 10 or its surroundings, susceptible to electric fields. The microtubules 22 positive charges are located at two centrioles 26 while two sets of negative poles are at a center 30 of the dividing cell 10 and point of attachment 34 of the microtubules 22** to the cell membrane. The locations of the charges form sets of double dipoles and therefore are susceptible to electric fields of differing directions. In one embodiment, the cells go through electroporation, that is, DNA or chromosomes are introduced into the cells using a pulse of electricity to briefly open pores in the cell membranes.

Turning now to FIG. 2, the TTFields described above that have been found to advantageously destroy tumor cells may be generated by an electronic apparatus 50. FIG. 2 is a simple schematic diagram of the electronic apparatus 50 illustrating major components thereof. The electronic apparatus 50 includes an electric field generator 54 operable connected to a transmitter circuitry 56 (described below in more detail). While the transmitter circuitry 56 is shown as separate from the electric field generator 54, in some embodiments, the transmitter circuitry 56 is integrated into one of the electric field generator 54 or a controller 74 (described below).

The electric field generator 54 includes circuitry configured to supply power and generate desirable electric signals (TTSignals) in the shape of waveforms or trains of pulses (e.g., an alternating current waveform) as an output. The transmitter circuitry 56 includes circuitry configured to supply a first wireless signal based on the output, i.e., first alternating current waveform) of the electric field generator 54. The first wireless signal is received by a receiver circuitry 58 and the receiver circuitry 58 has circuitry configured to convert the first wireless signal into a second alternating current waveform. The receiver circuitry 58 is in communication with a first transducer array 70*a* and a second transducer array 70*b*. Both of the first transducer array 70*a* and the second transducer array 70*b* are supplied with the second alternating current waveform (e.g., TTSignals). The first transducer array 70*a* and the second transducer array 70*b*, being supplied with the second alternating current waveform, causes an electrical current to flow between the first transducer array 70*a* and the second transducer array 70*b*. The electrical current generates an electric field (i.e., TTField), having a frequency and an amplitude, to be generated between the first transducer array 70*a* and the second transducer array 70*b*.

The electronic apparatus 50 may comprises one or more array set 72. While the electronic apparatus 50 shown in FIG. 2 comprises only a first array set 72*a* (i.e., the first transducer array 70*a* and the second transducer array 70*b*), in some embodiments, the electronic apparatus 50 may comprise more than two transducer arrays 70 and/or more than the first array set 72*a*. In one embodiment, each array set 72 comprises at least two transducer arrays 70 and the receiver circuitry 58.

The electric field generator 54 generates an alternating voltage wave form (i.e., TTSignal) at frequencies in the range from about 50 kHz to about 1 MHz (preferably from about 100 kHz to about 500 kHz). The required voltages are such that an electric field intensity in tissue within the treatment area is in the range of about 0.1 V/cm to about 10 V/cm. To achieve this electric field intensity, the potential difference between two conductors in the first transducer array 70*a* and the second transducer array 70*b* is determined by the relative impedances of the system components, e.g., a fraction of the electric field on each component is given by that component's impedance divided by a total circuit impedance.

In certain particular (but non-limiting) embodiments, the first transducer array 70*a* and the second transducer array 70*b* generate an alternating electric current and field within a target region of a patient. The target region typically comprises at least one tumor, and the generation of the alternating electric current and field selectively destroys and/or inhibits growth of the tumor. The alternating electric current and field may be generated at any frequency that selectively destroys or inhibits growth of the tumor, such as at any frequency of a TTField.

In certain particular (but non-limiting) embodiments, the alternating electric current and field may be imposed at two or more different frequencies. When two or more frequencies are present, each frequency is selected from any of the above-referenced values, or a range formed from any of the above-referenced values, or a range that combines two integers that fall between two of the above-referenced values.

In order to optimize the electric field (i.e., TTField) distribution, the first transducer array 70*a* and the second transducer array 70*b* (e.g., first array set 72*a*) may be configured differently depending upon the application in which the first array set 72*a* are to be used. In one embodiment, the first array set 72*a*, as described herein, is externally applied to a patient, that is, the transducer arrays 70 are generally applied to the patient's skin, in order to apply the electric current, and electric field (TTField) thereby generating current within the patient's tissue. Generally, the first array set 72*a* is placed on the patient's skin which may not include a wound or abrasion by a user such that the electric field is generated across patient tissue within a treatment area. TTFields that are applied externally can be of a local type or widely distributed type, for example, the treatment of skin tumors and treatment of lesions close to the skin surface.

In one embodiment, at least one of the first array set 72*a*, as described herein, is internally applied to the patient, that is, at least one transducer array 70 of the first array set 72*a* is applied beneath the skin of the patient, in order to apply the electric current, and electric field (TTField) thereby generating current within the patient's tissue. Generally, at least one transducer array 70 of the first array set 72*a* is placed under the skin of the patient, e.g., by a medical professional. If the other of the transducer array 70 of the first array set 72*a* is placed on the patient's skin, the user may place the other transducer array 70.

In one embodiment, the user may be a medical professional, such as a doctor, nurse, therapist, or other person acting under the instruction of a doctor, nurse, or therapist. In another embodiment, the user may be the patient, that is, the patient (and/or a helper) may place the first transducer array 70*a* and the second transducer array 70*b* on the patient's treatment area.

According to another exemplary embodiment, the electronic apparatus 50 includes the controller 74. In one embodiment, the controller 74 comprises circuitry configured to control the output of the electric field generator 54, for example, to set the output at the maximal value that does not cause excessive heating of the treatment area. The controller 74 may monitor the temperature of the treatment area with one or more temperature sensors, and may issue a warning, or the like, when a temperature of the treatment area exceeds a preset limit. The temperature sensors may be mechanically connected to and/or otherwise associated with the first transducer array 70*a* and/or the second transducer array 70*b* so as to sense the temperature of the treatment area at either one or both of the first transducer array 70*a* or the second transducer array 70*b*.

The first transducer array 70*a* and the second transducer array 70*b* may have specific shapes and positioning so as to generate the TTField of a desired configuration, direction, and intensity at the treatment area and only at that treatment area so as to focus the treatment.

In one embodiment, the controller 74 may turn off, or decrease power of the TTSignal generated by the electric field generator 54, if a temperature meets or exceeds a comfortability threshold. In one embodiment, the comfortability threshold is the temperature at which a patient would be made uncomfortable while using the first transducer array 70*a* and the second transducer array 70*b*. For example, the comfortability threshold may be a temperature at or about 41 degrees Celsius. In one embodiment, the comfortability threshold is a temperature of between about 39 degrees Celsius and 42 degrees Celsius, or a specific selected temperature between about 39 degrees Celsius and 42 degrees Celsius.

The specifications of the electronic apparatus 50 as a whole and its individual components are largely influenced by the fact that at the frequency of the TTFields, living systems behave according to their "Ohmic", rather than their dielectric properties.

Referring now to FIG. 3, shown therein is a diagram of an exemplary embodiment of the transducer array 70 constructed in accordance with the present disclosure. As shown in FIG. 3, each transducer array 70 is configured as a set of one or more electrode elements 78. In the example shown, the transducer array 70 includes 9 electrode elements 78. Transducer arrays 70 may utilize electrode elements 78 that are capacitively coupled. In the example shown in FIG. 3, the transducer array 70 is configured as multiple electrode elements 78 (for example, about 2 cm in diameter) that are interconnected via flex wires 80 (and connected to the electric field generator 54 via the receiver circuitry 58). In one embodiment, the transducer array 70 includes an outer peripheral edge 84.

In one embodiment, the transducer array 70 comprises at least one electrode element 78 having a first side and a second side, and a gel layer disposed on a first side of one or more of the electrode element 78. The transducer array 70 may further comprise a flexible top-coat layer in contact with, or attached to, the second side of the electrode element 78. The transducer array 70 may be constructed in accordance with a pad as described in U.S. patent application Ser. No. 17/813,837 filed on Jul. 20, 2022 and titled "CONDUCTIVE PAD GENERATING TUMOR TREATING FIELD AND METHODS OF PRODUCTION NAD USE THEREOF"; in accordance with U.S. patent application Ser. No. 17/810,062 filed on Jun. 30, 2022 and titled "TRANSDUCER ARRAY HAVING A VARIABLE RESISTANCE CONDUCTIVE GEL LAYER"; or in accordance with U.S. Patent Publication 2022/0288405 published on Sep. 15, 2022 and titled "ELECTRODE ARRAY AND METHODS OF PRODUCTION AND USE THEREOF", each of which is hereby incorporated herein in their entirety.

Figure 4:
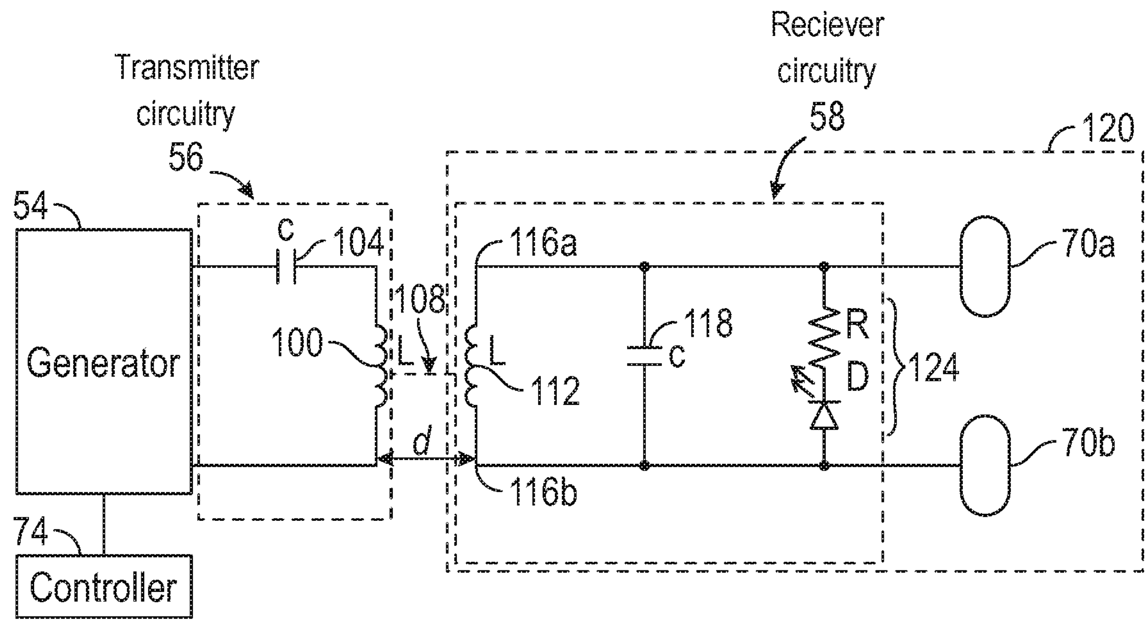
FIG. 4 is a schematic diagram of an exemplary embodiment of an assembly constructed in accordance with the present disclosure.

Referring now to FIG. 4, shown therein is a schematic diagram of an exemplary embodiment of the transmitter circuitry 56 in communication with the receiver circuitry 58 of FIG. 2. In FIG. 4, the transmitter circuitry 56 is in electrical communication with the electric field generator 54; however, in other embodiments, the transmitter circuitry 56 may be in communication with the controller 74.

In one embodiment, the transmitter circuitry 56 generally comprises a first inductor 100 in series with a first capacitor 104. The first inductor 100 may receive the first alternating current waveform, which, when passing through the first inductor 100, may generate a wireless signal 108.

It should be noted that the transmitter circuitry 56 has been shown for simplicity and additional electrical and/or electronic components may be included in the transmitter circuitry 56. For example, in some embodiments, the transmitter circuitry 56 may be a first transceiver circuitry, in which case, the first transceiver circuitry may include additional electrical/electronic components to receive a particular wireless signal.

In one embodiment, the receiver circuitry 58 may comprise a second inductor 112 having a first end 116*a* and a second end 116*b* and a second capacitor 118 configured in parallel with the second inductor 112. The first end 116*a* may further be in electrical communication with the first transducer array 70*a* while the second end 116*b* may further be in electrical communication with the second transducer array 70*b*.

The second inductor 112 of the receiver circuitry 58, receiving the wireless signal 108, may convert the wireless signal 108 into a second alternating current waveform having a same frequency as the first alternating current waveform and supply the second alternating current waveform to each of the first transducer array 70*a* and the second transducer array 70*b*. In this way, the first alternating current waveform generated by the electric field generator 54 may be wirelessly supplied to one or more of the transducer array 70, thereby reducing the need for a lead connected between the electric field generator 54 and each transducer array 70.

In one embodiment, the receiver circuitry 58 further includes, optionally, an indicator circuit 124. The indicator circuit 124 may be included to provide an indication that the receiver circuitry 58 is currently receiving the first wireless signal from the transmitter circuitry 56. In some embodiments, due to operation of the electronic apparatus 50, the patient may not otherwise have an indication that the electronic apparatus 50 is operating, e.g., causing the one or more transducer array 70 to generate a TTField. The indicator circuit 124 may thus provide confirmation of the current operation of the electronic apparatus 50, the electric field generator 54, and/or the transducer array 70.

It should be noted that the receiver circuitry 58 has been shown for simplicity and additional electrical and/or electronic components may be included in the receiver circuitry 58. For example, in some embodiments, the receiver circuitry 58 may be a second transceiver circuitry, in which case, the second transceiver circuitry may include additional electrical/electronic components to transmit a particular wireless signal. In other embodiments, the receiver circuitry 58 may be provided with one or more temperature sensor 125 for monitoring the temperature of the treatment area. In this embodiment, an output from the temperature sensor 125 can be supplied to an analog to digital converter, a microcontroller or other circuitry for generating data indicative of the temperature of at least a portion of the treatment area. The receiver circuitry 58 may also have a wireless transmitter configured to transmit the data indicative of the temperature to the controller 74 so that the controller 74 can monitor and control the power generated by the electric field generator 54 so as to maintain the temperature of the treatment area within acceptable limits.

In one embodiment, the first inductor 100 and the second inductor 112 are coupled to one another via one or more configuration and technique using magnetic fields to transfer the power. Exemplary techniques which can be used to transfer power from the first inductor 100 to the second inductor 112, include, for example, electromagnetic induction, magnetic resonance, electric field coupling, and/or radio reception. The wireless signal 102, then, may be transmitted from the first inductor 100 to the second inductor 112 via the coupling between the first inductor 100 and the second inductor 112. The particular configuration used may be determined by the transmission distance between the first inductor 100 and the second inductor 112, a desired efficiency of transmission of a signal between the first inductor 100 and the second inductor 112, and/or a medium through which the signal between the first inductor 100 and the second inductor 112 is transmitted. In one embodiment, the first inductor 100 and the second inductor 112 are inductively coupled, and, when connected with the first capacitor 104 and the second capacitor 118, forming a first LC circuit and a second LC circuit, respectively, may experience (e.g., exhibit) resonant inductive coupling. In this embodiment, the first capacitor 104 and the second capacitor 118 may be selected to induce a specific resonance frequency. In other embodiments, the transmitter circuitry 56 and the receiver circuitry 58 can be constructed using capacitive coupling techniques instead of inductive coupling. In this case, the transmitter circuitry 56 and the receiver circuitry 58 would include one or more pairs of spaced apart conductive electrodes for transferring electric fields between the transmitter circuitry 56 and the receiver circuitry 58. For example, the transmitter circuitry 56 and the receiver circuitry 58 can be constructed using monopolar coupling techniques or bipolar coupling techniques.

As used herein, the receiver circuitry 58 and any component connected to the receiver circuitry 58, such as the transducer arrays 70*a*-*b* or power circuitry 200 (described below) may be referred to herein as a remote device 120.

Figure 5:
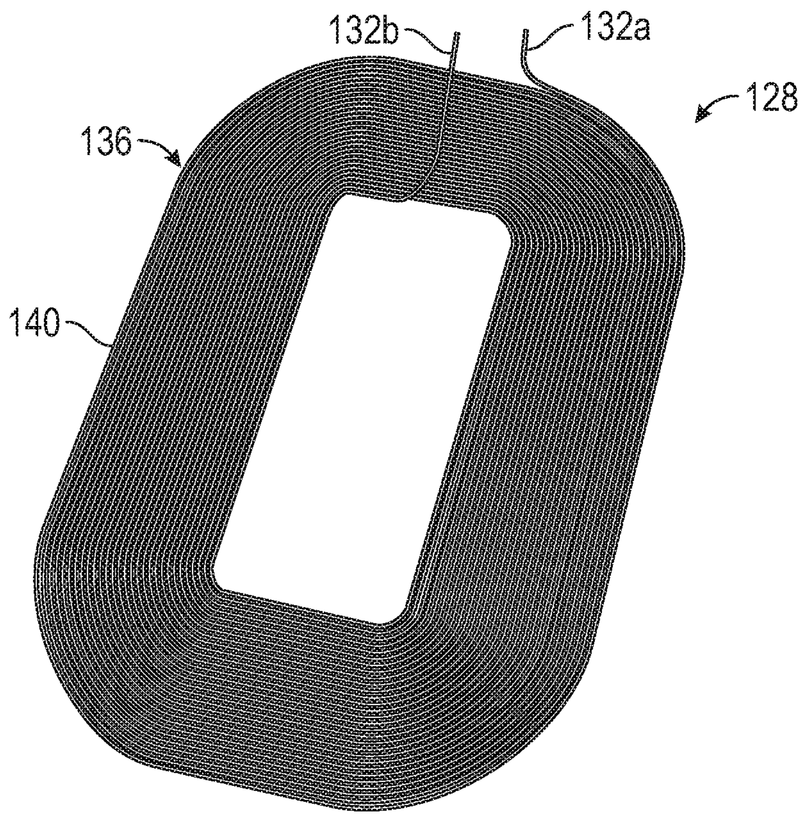
FIG. 5 is a diagram of an exemplary embodiment of an inductor constructed in accordance with the present disclosure.

Referring now to FIG. 5, shown therein is a schematic of an exemplary embodiment of an inductor 128 constructed in accordance with the present disclosure. The first inductor 100 and the second inductor 112 may be constructed in accordance with the construction of the inductor 128 discussed hereinafter. The inductor 128 comprises a first end 132*a*, a second end 132*b*, and a coil 136 formed by winding a conductor 140 fora selected number of turns thereby causing the inductor 128 to have particular electrical properties. Exemplary electrical properties for the inductor 128 may include an inductance, L, of 11.5-12 μH at frequencies between 50 kHz-1 MHz (e.g., at frequencies within the TTField range of frequencies), a Q-factor, Q, of about 130, a current rating, $I_R$, of about 8 A, a saturation current, $I_{SAT}$, of about 12 A, a DC resistance, $R_{DC}$, of between 56-68 mΩ, and a self-resonant frequency, $f_{res}$, of 12 MHz. An example of the inductor 128 may be an inductor of a WE-WPCC Wireless Power Array model number 760308104119 (Würth Elektronik, Waldenburg, Germany). The first end 132*a* of the inductor 128 may refer to one of the first end 116*a* and the second end 116*b* of the second inductor 112 while the second end 132*b* of the inductor 128 may refer to the other of the first end 116*a* or the second end 116*b* of the second inductor 112, when the second inductor 112 is implemented as the inductor 128, for example.

Referring back to FIG. 4, in some embodiments, the first inductor 100 and the second inductor 112, both constructed in accordance with the inductor 128 of FIG. 5, may be separated from one another by a distance, d. In some embodiments, the distance d may be between 0.25 inches and 0.5 inches. In some embodiments, the distance d may be between 0.25 inches and 10 yards.

In some embodiments, the transmitter circuitry 56 may transmit the wireless signal 108 at a first power and the wireless signal 108 is received by the receiver circuitry 58 at a second power. In the embodiment of FIG. 4, the electric field generator 54 and the transmitter circuitry 56 do not direct the wireless signal 108 in any particular direction. The difference between the first power and the second power may be dependent on the distance d, as described above, and any intervening objects between the transmitter circuitry 56 and the receiver circuitry 58. For example, if the wireless signal 108 is transmitted at 5 W, the receiver circuitry 58 may receive the wireless signal 108 having the second power of 0.5 W if the distance, d, is 10". Similarly, if the wireless signal 108 is transmitted at 50 W, the receiver circuitry 56 may receive the wireless signal 108 having the second power of 5 W if the distance, d, is 10", and if the wireless signal 108 is transmitted at 75 W, the receiver circuitry 58 may receive the wireless signal 108 having the second power of 7.5 W if the distance, d, is 10". Conversely, if the wireless signal 108 is transmitted at 5 W, the receiver circuitry 58 may receive the wireless signal 108 having the second power of 2.5 W if the distance, d, is 0.25", if the wireless signal 108 is transmitted at 15 W, the receiver circuitry 56 may receive the wireless signal 108 having the second power of 7.5 W if the distance, d, is 0.25", and if the wireless signal 108 is transmitted at 50 W, the receiver circuitry 58 may receive the wireless signal 108 having the second power of 25 W if the distance, d, is 0.25". In each of these examples, at both 0.25" and 10", there is no intervening object between the transmitter circuitry 56 and the receiver circuitry 58. In the embodiment of FIG. 5, the smaller the distance between the first inductor 100 and the second inductor 112, the larger the percent in power that is received by the second inductor 112. Therefore, it is advantageous to keep the first inductor 100 and the second inductor 112 closer together in order to maintain a higher power efficiency (e.g., a ratio between the second power over the first power approaches 1.0).

Figure 6A:
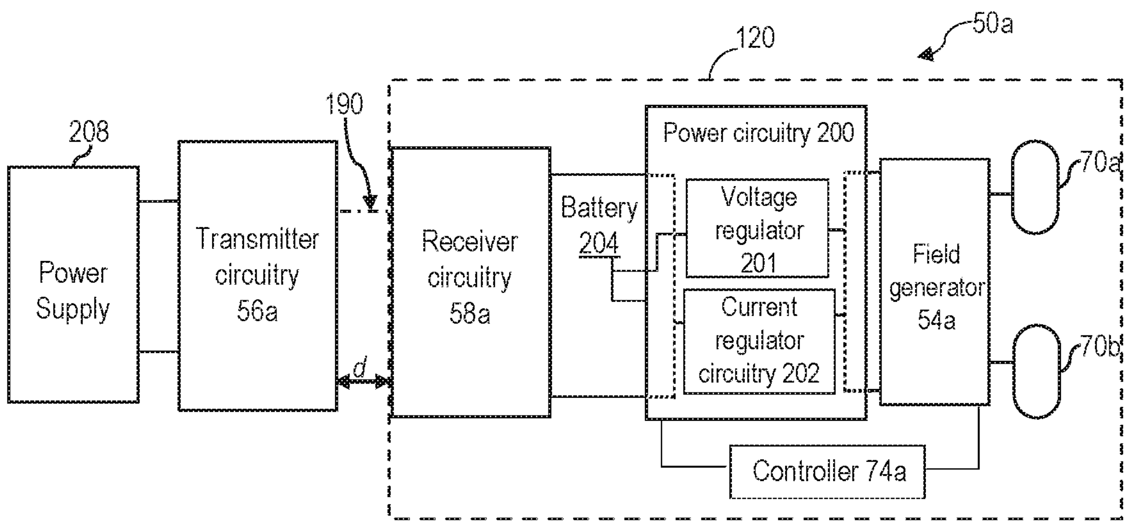
FIG. 6A is a schematic diagram of an exemplary embodiment of an assembly having an electric field generator on the receiver side of the assembly constructed in accordance with the present disclosure.

Referring now to FIG. 6A, shown therein is a schematic diagram of an exemplary embodiment of a first electronic apparatus 50*a* constructed in accordance with the present disclosure. The first electronic apparatus 50*a* differs from the electronic apparatus 50, described above, by receiving a wireless power signal 190 from a power supply 208 through the first transmitter circuitry 56*a* instead of the TTSignal and by including the power circuitry 200 disposed in a circuit between a first receiver circuitry 58*a* and the transducer arrays 70. The power supply 208 may be a traditional power supply connected to an electrical outlet, such as a residential electrical outlet and is operable to supply a first power to the first transmitter circuitry 56*a*.

In the first electronic apparatus 50*a*, the first transmitter circuitry 56*a* may be constructed in accordance with the transmitter circuitry 56 and the first receiver circuitry 58*a* may be constructed in accordance with the receiver circuitry 58.

The first electronic apparatus 50*a* further includes the power circuitry 200 disposed in a circuit between the first receiver circuitry 58*a* and the transducer arrays 70*a*-*b*. The power circuitry 200 may receive a power signal from the first receiver circuitry 58*a* and either provide the charging power to charge a battery 204 or power a first electric field generator 54*a* and a first controller 74*a*, or both charge the battery 204 and power the first electric field generator 54*a* and the first controller 74*a*. The first electric field generator 54*a* may have circuitry that receives power from the power circuitry 200 and generates an alternating current waveform, e.g., based on an instruction and/or a TTSignal from the first controller 74*a*, wherein the alternating current waveform, when received by the transducer arrays 70*a*-*b*, causes the transducer arrays 70*a*-*b* to generate the TTField.

The power circuitry 200 comprises power control circuitry that may receive a first power and selectively provide the charging power to the battery 204, e.g., in order to charge the battery 204, and provide a third power to the first electric field generator 54*a*. The power circuitry 200 may receive the first power from one or more of the first receiver circuitry 58*a* or the battery 204, or both. For example, when insufficient power is received by the first receiver circuitry 58*a* to operate the transducer arrays 70*a*-*b*, the power circuitry 200 may supplement the insufficient power with power derived from the battery 204. As such, the power circuitry 200 may include a voltage regulator 201 to amplify the voltage from the battery 204 to a voltage supplied to the transducer arrays 70*a*-*b*. Additionally, or alternatively, the power circuitry 200 may include the voltage regulator 201 to reduce a voltage received from the first receiver circuitry 58*a* to both a TTSignal voltage transmitted to the transducer arrays 70*a*-*b* and a battery charging voltage transmitted to the battery 204 to charge (or trickle-charge) the battery 204.

In this embodiment, the patient can move about their environment unencumbered by the first electric field generator 54*a* being plugged into a stationary power supply, such as an electrical outlet. Advantageously, as the patient moves about their environment, when the patient comes within range of the wireless power signal 190, the first electronic apparatus 50*a* can start to charge the battery 204 without any intervention from the patient. For example, the patient may place the first transmitter circuitry 56*a* near their commonly used living room recliner such that, when the patient is resting in the recliner, the battery 204 is being charged without the patient doing anything more than sitting in a chair.

Figure 6B:
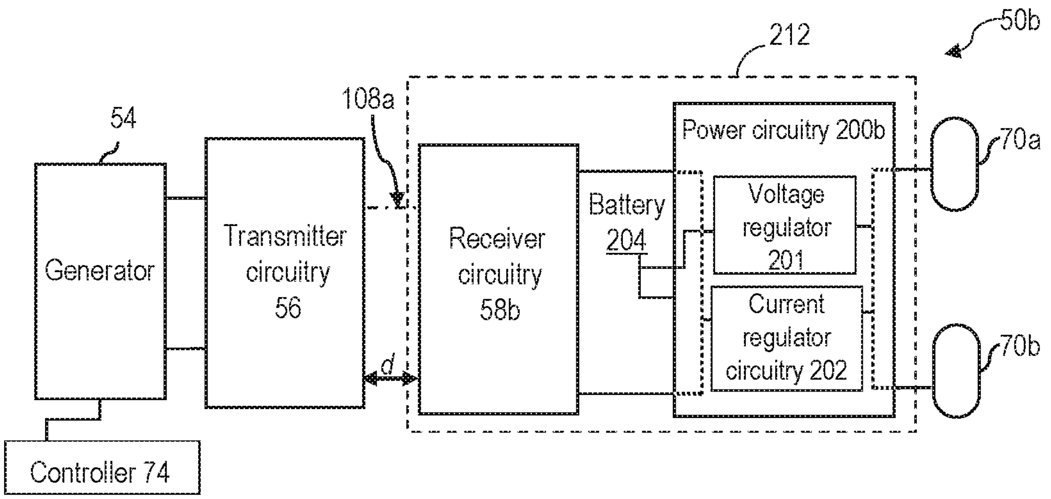
FIG. 6B is a schematic diagram of an exemplary embodiment of an assembly having a power circuitry constructed in accordance with the present disclosure.

Referring now to FIG. 6B, shown therein is a schematic diagram of an exemplary embodiment of a second electronic apparatus 50*b* constructed in accordance with the present disclosure. The second electronic apparatus 50*b* differs from the electronic apparatus 50, described above, by including a second power circuitry 200*b* disposed between a second receiver circuitry 58*b* and the transducer arrays 70.

Generally, the transmitter circuitry 56 transmits a first TTSignal, having a first power and a first frequency, as a variable wireless signal 108*a* to the second receiver circuitry 58*b*. The second receiver circuitry 58*b* may receive the variable wireless signal 108*a* and convert the variable wireless signal 108*a* to a second TTSignal having a second power and the first frequency. The second power circuitry 200*b*, receiving the second TTSignal, may comprise a voltage regulator 201 and a current regulator circuitry 202 operable to transform (e.g., amplify) the second TTSignal, having the second power, to an applied TTSignal having a third power and the first frequency. The third power may be greater than the second power and generally is between 20 W and 40 W but may be between 10 W and 84 W.

It should be noted that the variable wireless signal 108*a* is referred to as "variable" because, as a patient moves around in their environment, a power transmitted over a wireless signal 108 may vary significantly. Importantly, the TTSignal that is transmitted from the transmitter circuitry 56 to the second receiver circuitry 58*b* has the waveform as generated by the electric field generator 54, even if power of the waveform is not provided at therapeutic levels.

In one embodiment, the transmitter circuitry 56 transmits the first TTSignal to the receiver circuitry 58 as the variable wireless signal 108*a*. The second receiver circuitry 58*b* may convert the variable wireless signal 108*a* into the second TTSignal, which is, in turn, received by the second power circuitry 200*b*. The second power circuitry 200*b* may amplify the second TTSignal, supplementing the second power of the second TTSignal with power drawn from the battery 204.

In this embodiment, the transmitter circuitry 56 may not transmit the variable wireless signal 108*a* with enough power to meet a power needed for the TTSignal supplied to the transducer arrays 70*a-b*. In this case, in some embodiments, the second power circuitry 200*b* may only include circuitry to draw power from the battery 204, excluding circuitry to charge the battery 204.

In one embodiment, when the battery 204 reaches a low power threshold, the second electronic apparatus 50*b* enters a battery charging mode, thereby causing the second power circuitry 200*b* to charge the battery 204 instead of providing a TTSignal to the transducer arrays 70*a-b*. In other embodiments, when the battery 204 reaches the low power threshold, the second electronic apparatus 50*b* provides a notification to the patient that the battery 204 is low on power and needs to be recharged. In this embodiment, the second electronic apparatus 50*b* may, or may not, continue to provide the TTSignal to the transducer arrays 70*a-b*, albeit at a lower power than may otherwise be ideal.

In one embodiment, when the patient receives the notification that the battery 204 has a low power, the patient may disconnect the battery 204 and connect the battery 204 directly to a charger separate from the second electronic apparatus 50*b*. In other embodiments, when the patient receives the notification that the battery 204 has a low power, the patient may remove the second receiver circuitry 58*b*, the second power circuitry 200*b*, the battery 204 (collectively, a receiver module 212), and the transducer array(s) 70 connected to the battery 204, and replace all of the above (e.g., with a different, new, and/or unopened one of the receiver module 212 and transducer array(s) 70).

In one embodiment, the receiver module 212 may include a housing 216 to support the second receiver circuitry 58*b*, the second power circuitry 200*b*, and the battery 204. In this way. The transducer array(s) 70 may be disconnected from the receiver module 212 when the transducer array(s) 70 need to be replaced. In some embodiment, the receiver module 212 may allow for selective removal of the battery 204, such as to recharge the battery 204 in a separate charger or to replace the battery 204, e.g., with a battery 204 having a full charge.

While the receiver module 212 is shown as being connected to two transducer arrays 70*a-b*, it should be understood that in other embodiments, the receiver module 212 may be connected to more than two transducer arrays 70. The number of transducer arrays 70 attached to the receiver module 212 may be dependent on a number of transducer arrays 70 applied to the patient, e.g., by a doctor. Additionally, the number of transducer arrays 70 attached to the receiver module 212 may be dependent on a power capacity of the battery 204 and a duration for applying the TTFields to the patient—that is, as more transducer arrays 70 applying TTFields to the patient requires additional power, the duration of TTField treatment and the power capacity of the battery 204 may restrict the number of transducer arrays 70 powered by the battery 204 of the receiver module 212.

In one embodiment, the battery 204 provides approximately 3.7 V with a power capacity of about 5000 mAH. In other embodiments, the battery may provide about 3.85 V with a power capacity of about 11.78 Wh.

Figure 6C:
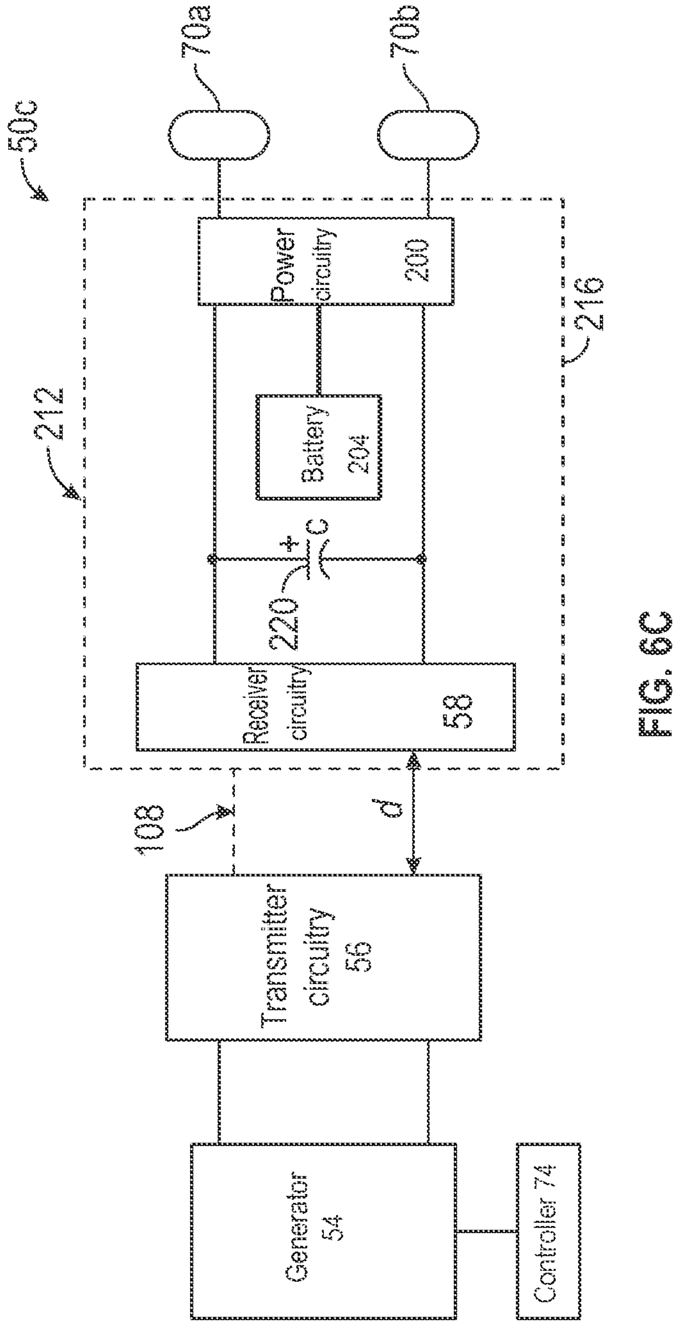
FIG. 6C is a schematic diagram of an exemplary embodiment of an assembly having a supercapacitor circuitry constructed in accordance with the present disclosure.

Referring now to FIG. 6C, shown therein is a schematic diagram of an exemplary embodiment of a third electronic apparatus 50*c* constructed in accordance with the present disclosure. The third electronic apparatus 50*c* differs from the electronic apparatuses 50*a-b*, described above, by including a supercapacitor 220 operable to receive power from the wireless signal 108 in a short period of time and discharge that power into the power circuitry 200 to supply power to both charge the battery 204 and supply power to the transducer array(s) 70 as described above in more detail. In this embodiment, the power circuitry 200 may be further configured to accommodate a voltage drop when the supercapacitor 220 is discharged due to a large internal resistance in the supercapacitor 220.

Figure 7:
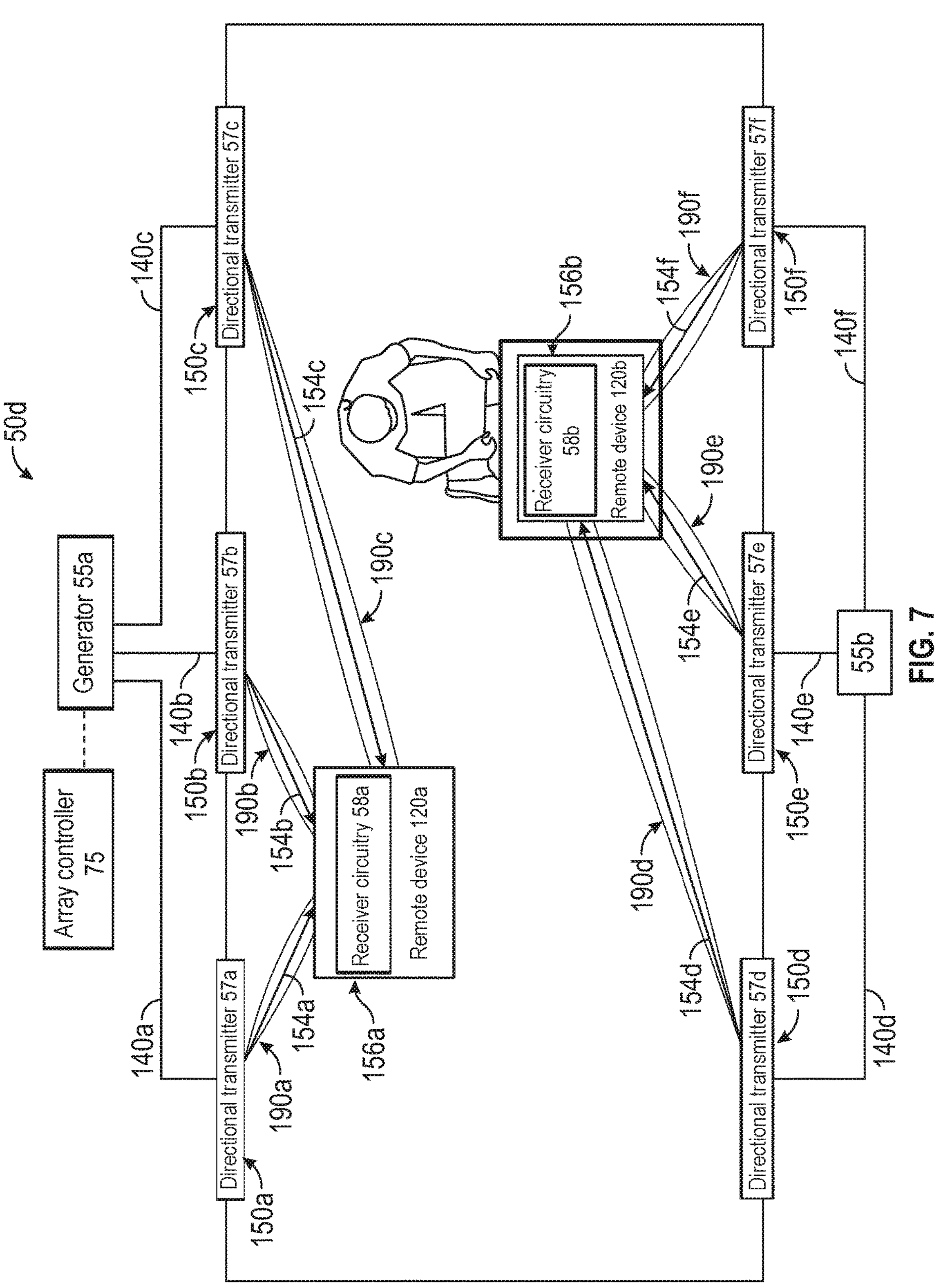
FIG. 7 is a diagram of two aspects of an exemplary embodiment of the assembly in use in accordance with the present disclosure.

Referring now to FIG. 7, shown therein is a diagram of a fourth electronic apparatus 50*d* supplying power utilizing a far-field transmission technique and constructed in accordance with the present disclosure. Generally, the fourth electronic apparatus 50*d* includes an array controller 75, a first generator 55*a*, a plurality of directional transmitters 57 (labeled in FIG. 7 with the reference numerals 57*a*, 57*b* and 57*c*), and a remote device 120. The array controller 75 communicates with the generator 55*a* to cause the generator 55*a* to supply a particular power signal 140*a-n* to each of a plurality of directional transmitters 57. Each directional transmitter 57 then transmits a wireless power signal 190*a-n* directed towards the remote device 120.

The remote device 120 is shown in more detail in FIG. 6A. As described above, the remote device 120 includes the receiver circuitry 58. In this embodiment, the first receiver circuitry 58*a* may be constructed to receive one or more power signals based upon a far-field or radiative transmission technique such as those described below.

In one embodiment, each directional transmitter 57 is constructed using (e.g., configured to conform to) far-field or radiative techniques, which may also be referred to as power beaming. In these techniques, power is transferred by beams of electromagnetic radiation which may be in the form of microwaves or laser beams, for example. When a particular directional transmitter 57 is configured to transmit power via microwaves, the microwaves can be generated and aimed using phase array techniques and received by the first receiver circuitry 58*a*, which may include a rectenna, for example. When a particular directional transmitter 57 is configured to transmit power via laser beams, the laser beams can be generated and aimed towards the first receiver circuitry 58*a* of the remote device 120. The first receiver circuitry 58*a*, in these embodiments, may comprise a photoreceiver, a photodiode, phototransistor, or one or more arrays thereof, for example. In any event, all of these techniques are configured to transport energy longer distances than can be practically transported using magnetic fields or electric fields. But, the directional transmitter(s) 57 must be aimed at the first receiver circuitry 58*a* of the remote device 120.

In the first aspect shown in FIG. 7, a first generator 55*a* is electrically coupled to a plurality of directional transmitters 57, e.g., the first generator 55*a* transmits: a first power signal 140*a* to a first directional transmitter 57*a*; a second power signal 140*b* to a second directional transmitter 57*b*; and a third power signal 140*c* to a third directional transmitter 57*c*. The first directional transmitter 57*a* at a first transmitter location 150*a* may generate a first wireless power signal 190*a* having a first power directed along a first vector 154*a* based on the first power signal 140*a*; the second directional transmitter 57*b* at a second transmitter location 150*b* may generate a second wireless power signal 190*b* having a second power directed along a second vector 154*b* based on the second power signal 140*b*; and the third directional transmitter 57*c* at a third transmitter location 150*c* may generate a third wireless power signal 190*c* having a third power directed along a third vector 154*c* based on the third power signal 140*c*. The first vector 154*a* may extend (e.g., originate) from the first transmitter location 150*a* to the first receiver circuitry 58*a* of the first remote device 120*a* at a first receiver location 156*a*, the second vector 154*b* may extend from the second transmitter location 150*b* to the first receiver circuitry 58*a*, and the third vector 154*c* may extend from the third transmitter location 150*c* to the first receiver circuitry 58*a*.

In one embodiment of the first aspect, each of the first directional transmitter 57*a*, the second directional transmitter 57*b*, and the third directional transmitter 57*c* may further be in electrical communication with the array controller 75. The array controller 75 may determine the first power in the first vector 154*a*, the second power in the second vector 154*b*, and the third power in the third vector 154*c*. The array controller 75 may further cause the first directional transmitter 57*a*, the second directional transmitter 57*b*, and the third directional transmitter 57*c* to generate each, respective wireless power signal 190*a-c*. In some embodiments, the directional transmitters 57 comprise a plurality of transmitters and the array controller 75, by controlling each directional transmitters 57*a-c*, may further control each of the plurality of transmitters of each directional transmitter 57*a-c*.

In this way, the array controller 75 may direct power to one or more remote device 120 (such as the first remote device 120*a*) with a higher accuracy and/or efficiency by beamforming the wireless power signal 190*a-c* through a combination of the first wireless power signal 190*a*, the second wireless power signal 190*b*, and the third wireless power signal 190*c*.

In a second aspect shown in FIG. 7, a second generator 55*b* is in communication with a plurality of directional transmitters 57, e.g., the second generator 55*b* transmits: a fourth power signal 140*d* to a fourth directional transmitter 57*d*; a fifth power signal 140*e* to a fifth directional transmitter 57*e*; and a sixth power signal 140*f* to a sixth directional transmitter 57*f*. Each directional transmitter 57*d-f* is configured to transmit power to the receiver circuitry (such as first receiver circuitry 58*a* and second receiver circuitry 58*b*) of a second remote device 120*b* at a second receiver location 156*b*. The fourth directional transmitter 57*d* at a fourth transmitter location 150*d* may generate a fourth wireless power signal 190*d* having a fourth power directed along a fourth vector 154*d*, the fifth directional transmitter 57*e* at a fifth transmitter location 150*e* may generate a fifth wireless power signal 190*e* having a fifth power directed along a fifth vector 154*e*, and the sixth directional transmitter 57*f* at a sixth transmitter location 150*f* may generate a sixth wireless power signal 190*f* having a sixth power directed along a sixth vector 154*f*. The fourth vector 154*d* may extend from the fourth transmitter location 150*d* to the first receiver circuitry 58*a* of the second remote device 120*b*, the fifth vector 154*e* may extend from the fifth transmitter location 150*e* to the first receiver circuitry 58*a* of the second remote device 120*b*, and the sixth vector 154*f* may extend from the sixth transmitter location 150*f* to the first receiver circuitry 58*a* of the second remote device 120*b*. The first receiver circuitry 58*a* may be electrically connected to one or more of the electric field generator 54 and/or the controller 74 within the second remote device 120*b*.

In some embodiments of the second aspect shown in FIG. 7, the receiver circuitry 58*a*, 58*b* may be electrically connected to a power circuitry 200 of the remote device 120, described in detail above in FIG. 6A. The fourth wireless power signal 190*d*, the fifth wireless power signal 190*e*, and the sixth wireless power signal 190*f* may be configured to provide electrical power to the power circuitry 200, which may, in turn, provide a charging power to charge a battery 204, power two or more transducer arrays 70, transmit a secondary wireless signal from a first transmitter circuitry 56*a* to the first receiver circuitry 58*a* (e.g., in accordance with transmission of the wireless signal 108 from the transmitter circuitry 56 to the receiver circuitry 58 as shown in FIG. 4), and/or the like.

Figure 8:
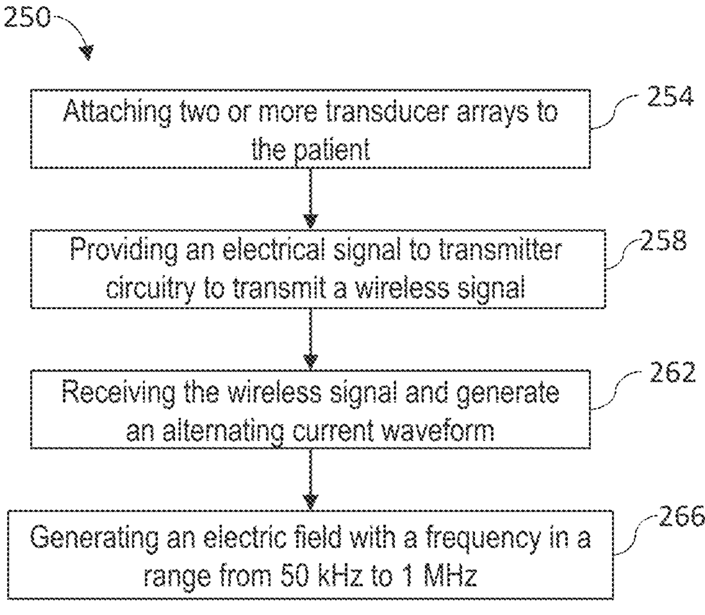
FIG. 8 is a process flow diagram of a process for using the assembly in accordance with the present disclosure.

Referring now to FIG. 8, shown therein is an exemplary embodiment of a process 250 of applying a TTField to a patient in accordance with the present disclosure. The process 250 generally comprises the steps of: attaching two or more transducer arrays to the patient (step 254); providing a first signal to a transmitter circuitry to transmit a wireless signal (step 258); receiving the wireless signal by a receiver circuitry and generating an alternating current waveform (step 262); and generating an alternating electric field having a frequency in a range of from about 50 kHz to about 1 MHz (step 266).

In one embodiment, attaching two or more transducer arrays to the patient (step 254) includes placing the two or more transducer arrays 70 at predetermined locations on the patient. In some embodiments, the first transducer array 70*a* may be placed at a first target location on the patient and the second transducer array 70*b* may be placed at a second target location on the patient.

In one embodiment, attaching two or more transducer arrays to the patient (step 254) may be performed by the user (or a helper), or a person under the instruction of the user or a medical professional. In one embodiment, before placing the transducer arrays 70 on the patient, the patient may need to be cleaned (e.g., such as but not limited to, cleansing of the skin of foreign matter or biological matter and shaving of the skin, if necessary) to enable the transducer arrays 70 to adhere to the patient.

In one embodiment, attaching two or more transducer arrays to the patient (step 254) may include placing the first transducer array 70*a* at a first target location subdermally and the second transducer array 70*b* may be placed at the second target location on the patient's skin.

In one embodiment, providing the electric signal to the transmitter circuitry to transmit the wireless signal (step 258) includes causing the electric field generator 54 to generate the electrical signal wherein the first signal is supplied to the transmitter circuitry 56. The transmitter circuitry 56 generates and transmits the wireless signal based on the electrical signal.

In one embodiment, providing the electrical signal to the transmitter circuitry to transmit the wireless signal (step 258) includes generating, by the electric field generator 54, an alternating current waveform as the electrical signal. In other embodiments, providing the electrical signal to the transmitter circuitry to transmit the wireless signal (step 258) includes generating a wireless power signal as the electrical signal.

In one embodiment, receiving the wireless signal by the receiver circuitry and generating the alternating current waveform (step 262) includes receiving the wireless signal and converting the wireless signal into the alternating current waveform, when the wireless signal was generated by the electrical signal being the alternating current waveform.

In one embodiment, receiving the wireless signal by the receiver circuitry and generating the alternating current waveform (step 262) includes receiving the wireless power signal and using, by the power circuitry 200, a supplied power from the wireless power signal to charge a battery, power an electric field generator to generate a TTSignal having an alternating current waveform within a frequency range from 50 KHz to 1 MHz, and provide the alternating current waveform to the two or more transducer arrays 70, or some combination thereof such that the transducer arrays 70 generate and supply a TTField to a patient.

In one embodiment, receiving the wireless signal by the receiver circuitry and generating the alternating current waveform (step 262) includes generating the alternating current waveform by the first electric field generator 54*a* electrically coupled to the power circuitry 200. The first electric field generator 54*a* may be powered by one or more of the battery 204 or the supplied power from the wireless power signal.

In one embodiment, generating an alternating electric field having a frequency in a range of from about 50 kHz to about 1 MHz (step 266).

The step of generating an alternating electric field (TTField) (step 266) may be performed by providing the alternating current waveform to the two or more transducer arrays 70, such as the first transducer array 70*a* and the second transducer array 70*b*.

In one embodiment, step 266 may be performed more than one time and the period of time for which the step 266 is performed a first time may be the same as or different from the period of time for which the step 266 is performed a second time (or other period(s) of time beyond the second time).

In some embodiments, step 266 is only performed once before the process 250 is repeated. There may be a time period between each time the process 250 is repeated. Each time the process 250 is repeated, the time period may be the same as or different from the previous time period. Each time the process 250 is repeated, the first electrode and the second electrode may be placed in the same or a different target location.

The step of generating an alternating electric field (TTField) (step 266) may be performed by generating the alternating current waveform and field at two or more different frequencies within the range of 50 kHz to 1 MHz. When two or more frequencies are present, each frequency is selected from any of the above-referenced values, or a range formed from any of the above-referenced values, or a range that combines two integers that fall within the range of the above-referenced values.

In one embodiment, the step of generating an alternating electric field (TTField) (step 266) may be performed by supplying a first alternating current waveform and field to a first pair of transducer arrays 70 for a first period of time and supplying a second alternating current waveform and field to a second pair of transducer arrays 70 for a second period of time. In one embodiment, the first period of time may be of a similar duration to the second period of time whereas in other embodiments, the first period of time may be of a different duration to the second period of time. Additionally, the first period of time may or may not overlap with the second period of time.

ILLUSTRATIVE EMBODIMENTS

Various features and advantages of the disclosure are set forth in the following numbered illustrative embodiments:

Illustrative Embodiment 1. A system, comprising:
- an electric field generator configured to generate a first electrical signal having an alternating current waveform at a frequency in a range from 50 kHz to 1 MHz;
- a transmitter circuitry electrically coupled to the electric field generator and operable to receive the first electrical signal and transmit a wireless signal;
- a receiver circuitry operable to receive the wireless signal and output a second electrical signal having the alternating current waveform;
- a first transducer array electrically coupled to the receiver circuitry; and
- a second transducer array electrically coupled to the receiver circuitry;
- wherein the first transducer array and the second transducer array are configured to generate an alternating electric field based on the alternating current waveform of the second electrical signal received from the receiver circuitry.

Illustrative Embodiment 2. The system of Illustrative Embodiment 1, wherein the transmitter circuitry comprises a first inductor and the receiver circuitry comprises a second inductor, the second inductor being inductively coupled to the first inductor.

Illustrative Embodiment 3. The system of Illustrative Embodiment 2, wherein the transmitter circuitry further comprises a first LC circuit having a first capacitor electrically connected to the first inductor; and the receiver circuitry further comprises a second LC circuit having a second capacitor electrically coupled to the second inductor, the first LC circuit and the second LC circuit configured to exhibit resonant inductive coupling.

Illustrative Embodiment 4. The system of Illustrative Embodiment 3, wherein the first capacitor and the second capacitor are selected to induce resonant inductive coupling between the first LC circuit and the second LC circuit at a resonant frequency.

Illustrative Embodiment 5. The system of Illustrative Embodiment 4, wherein the resonant frequency is the frequency of the alternating current waveform.

Illustrative Embodiment 6. The system of Illustrative Embodiments 1-5, wherein the alternating current waveform has a first power, further comprising: a power circuitry operable to receive the alternating current waveform and amplify the first power of the alternating current waveform to a second power, the power circuitry electrically disposed between the receiver circuitry and each of the first transducer array and the second transducer array.

Illustrative Embodiment 7. The system of Illustrative Embodiment 6, further comprising: a battery having a power capacity and coupled to the power circuitry, the battery operable to provide a third power to the power circuitry; and wherein the power circuitry is further operable to selectively amplify the first power of the alternating current waveform to the second power by using a portion of the third power.

Illustrative Embodiment 8. The system of Illustrative Embodiment 7, wherein the battery is further operable to receive a charging power to charge the battery, and wherein the power circuitry is further operable to selectively provide the charging power to the battery from the first power of the alternating current waveform.

Illustrative Embodiment 9. A system, comprising:

a power supply operable to supply a first power;

a transmitter circuitry electrically coupled to the power supply and operable to transmit a wireless power signal based on the first power;

a receiver circuitry operable to receive the wireless power signal and output a second power;

an electric field generator configured to receive the second power and generate an alternating current waveform at a frequency in a range from 50 kHz to 1 MHz;

a first transducer array electrically coupled to the electric field generator; and a second transducer array electrically coupled to the electric field generator;

wherein the first transducer array and the second transducer array are configured to generate an alternating electric field based on the alternating current waveform received from the electric field generator.

Illustrative Embodiment 10. The system of Illustrative Embodiment 9, wherein the receiver circuitry is operable to output at least a portion of the first power; and further comprising: a power circuitry operable to receive the portion of the first power and amplify the portion of the first power to the second power, the power circuitry electrically disposed between the receiver circuitry and the electric field generator.

Illustrative Embodiment 11. The system of Illustrative Embodiment 10, further comprising: a battery having a power capacity and coupled to the power circuitry, the battery operable to provide a third power to the power circuitry; and wherein the power circuitry is further operable to selectively amplify the portion of the first power and the third power to the second power.

Illustrative Embodiment 12. The system of Illustrative Embodiment 11, wherein the battery is further operable to receive a charging power to charge the battery, and wherein the power circuitry is further operable to selectively provide the charging power to the battery from the portion of the first power.

Illustrative Embodiment 13. The system of Illustrative Embodiments 9-12, wherein the transmitter circuitry comprises a first inductor and the receiver circuitry comprises a second inductor, the second inductor being inductively coupled to the first inductor.

Illustrative Embodiment 14. The system of Illustrative Embodiment 13, wherein the transmitter circuitry further comprises a first LC circuit having a first capacitor electrically connected to the first inductor; and the receiver circuitry further comprises a second LC circuit having a second capacitor electrically coupled to the second inductor, the first LC circuit and the second LC circuit exhibiting resonant inductive coupling.

Illustrative Embodiment 15. The system of Illustrative Embodiment 14, wherein the first capacitor and the second capacitor are selected to induce resonant inductive coupling between the first LC circuit and the second LC circuit at a resonant frequency.

Illustrative Embodiment 16. The system of Illustrative Embodiments 9-15, wherein the transmitter circuitry is a directional transmitter configured to conform to a far-field transmission technique.

Illustrative Embodiment 17. The system of Illustrative Embodiment 16, wherein the directional transmitter is a first directional transmitter, and the wireless power signal is a first wireless power signal; and further comprising:

a second directional transmitter configured to conform to the far-field transmission technique, the second directional transmitter being electrically coupled to the power supply and operable to transmit a second wireless power signal based on the first power; and wherein the receiver circuitry is further operable to receive the first wireless power signal and the second wireless power signal; generate the second power based on at least a first portion of the first power received from the first wireless power signal and at least a second portion of the first power received from the second wireless power signal.

Illustrative Embodiment 18. The system of Illustrative Embodiment 17, wherein the receiver circuitry is at a receiver location, and further comprising:

the first directional transmitter placed at a first location and further operable to transmit the first wireless power signal as a first beam directed along a first vector, the first vector originating at the first location and directed to the receiver location; and the second directional transmitter placed at a second location and further operable to transmit the second wireless power signal as a second beam directed along a second vector, the second vector originating at the second location and directed to the receiver location;

wherein the first vector and the second vector are different.

Illustrative Embodiment 19. A method, comprising:

providing a first electrical signal to a transmitter circuitry, the transmitter circuitry configured to transmit a wireless signal based on the first electrical signal;

receiving the wireless signal by a receiver circuitry, the receiver circuitry operable to receive the wireless signal and generate a second electrical signal;

transmitting the second electrical signal to two or more transducer arrays applied to a patient; and generating an electric field based on the second electrical signal between the two or more transducer arrays, the second electrical signal having a frequency in a range between 50 kHz-1 MHz.

Illustrative Embodiment 20. The method of Illustrative Embodiment 19, further comprising: generating an alternating current waveform having the frequency in the range between 50 kHz-1 MHz for a period of time; and wherein generating the alternating current waveform is performed prior to providing the first electrical signal, and wherein the first electrical signal includes the alternating current waveform.

Illustrative Embodiment 21. The method of Illustrative Embodiment 19, further comprising: generating an alternating current waveform having the frequency in the range between 50 kHz-1 MHz for a period of time; and wherein generating the alternating current waveform is performed after receiving the wireless signal, and wherein the second electrical signal includes the alternating current waveform.

Illustrative Embodiment 22. The method of Illustrative Embodiments 19-21, wherein the transmitter circuitry comprises a first inductor and the receiver circuitry comprises a second inductor; and further comprising: coupling, resonantly, the first inductor of the transmitter circuitry and the second inductor of the receiver circuitry.

From the above description, it is clear that the inventive concepts disclosed and claimed herein are well adapted to carry out the objects and to attain the advantages mentioned herein, as well as those inherent in the disclosure. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features and steps are recited in the claims and/or disclosed in the specification, these combinations are not intended to limit the disclosure. In fact, many of these features and steps may be combined in ways not specifically recited in the claims and/or disclosed in the specification. Although each dependent claim listed below may directly depend on only one other claim, the disclosure includes each dependent claim in combination with every other claim in the claim set.

Similarly, although each illustrative embodiment listed above may directly depend on only one other illustrative embodiment, the disclosure includes each illustrative embodiment in combination with every other illustrative embodiment in the set of illustrative embodiments for each mode of the inventive concepts disclosed herein.

No element, act, or instruction used in the present application should be construed as critical or essential to the disclosure unless explicitly described as such outside of the preferred embodiment. Further, the phrase "based on" is intended to mean "based, at least in part, on" unless explicitly stated otherwise.

What is claimed is:

1. A system, comprising:

an electric field generator configured to generate a first electrical signal having an alternating current waveform at a frequency in a range from 50 KHz to 1 MHz;

a transmitter circuitry electrically coupled to the electric field generator and operable to receive the first electrical signal and transmit a wireless signal that comprises the first electrical signal from the electric field generator;

a receiver circuitry operable to receive the wireless signal comprising the first electrical signal and output a second electrical signal having the alternating current waveform of the first electrical signal from the electric field generator;

a first transducer array electrically coupled to the receiver circuitry; and a second transducer array electrically coupled to the receiver circuitry;

wherein the first transducer array and the second transducer array are configured to generate an alternating electric field based on the alternating current waveform of the second electrical signal received from the receiver circuitry.

2. The system of claim 1, wherein the transmitter circuitry comprises a first inductor and the receiver circuitry comprises a second inductor, the second inductor being inductively coupled to the first inductor.

3. The system of claim 2, wherein the transmitter circuitry further comprises a first LC circuit having a first capacitor electrically connected to the first inductor; and the receiver circuitry further comprises a second LC circuit having a second capacitor electrically coupled to the second inductor, the first LC circuit and the second LC circuit configured to exhibit resonant inductive coupling.

4. The system of claim 3, wherein the first capacitor and the second capacitor are selected to induce resonant inductive coupling between the first LC circuit and the second LC circuit at a resonant frequency.

5. The system of claim 4, wherein the resonant frequency is the frequency of the alternating current waveform.

6. The system of claim 1, wherein the alternating current waveform has a first power, further comprising:

a power circuitry operable to receive the alternating current waveform and amplify the first power of the alternating current waveform to a second power, the power circuitry electrically disposed between the receiver circuitry and each of the first transducer array and the second transducer array.

7. The system of claim 6, further comprising:

a battery having a power capacity and coupled to the power circuitry, the battery operable to provide a third power to the power circuitry; and wherein the power circuitry is further operable to selectively amplify the first power of the alternating current waveform to the second power by using a portion of the third power.

8. The system of claim 7, wherein the battery is further operable to receive a charging power to charge the battery, and wherein the power circuitry is further operable to selectively provide the charging power to the battery from the first power of the alternating current waveform.

9. A method, comprising:

providing a first electrical signal having an alternating current waveform at a frequency in a range from 50 KHz to 1 MHz to a transmitter circuitry, the transmitter circuitry configured to transmit a wireless signal comprising the first electrical signal;

receiving the wireless signal from the transmitter circuitry comprising the first electrical signal having the alternating current waveform at the frequency in the range from 50 kHz to 1 MHz by a receiver circuitry, the receiver circuitry operable to receive the wireless signal and generate a second electrical signal;

transmitting the second electrical signal having the alternating current waveform at the frequency in the range from 50 kHz to 1 MHz to two or more transducer arrays applied to a patient; and generating an electric field based on the second electrical signal between the two or more transducer arrays, the second electrical signal having the frequency in the range from 50 kHz to 1 MHz.

10. The method of claim 9, wherein the transmitter circuitry comprises a first inductor and the receiver circuitry comprises a second inductor; and further comprising:

coupling, resonantly, the first inductor of the transmitter circuitry and the second inductor of the receiver circuitry.

* * * * *